(12) United States Patent
Goldstein et al.

(10) Patent No.: US 8,232,304 B2
(45) Date of Patent: Jul. 31, 2012

(54) ANTIFUNGAL FORMULATIONS

(75) Inventors: Jay A. Goldstein, Newton, MA (US);
Michael Rothman, Newton, MA (US);
Whe-Yong Lo, Canton, MA (US)

(73) Assignee: G & R Pharmaceuticals, LLC, Newton, MA (US)

( * ) Notice: Subject to any disclaimer, the term of this patent is extended or adjusted under 35 U.S.C. 154(b) by 2031 days.

(21) Appl. No.: 10/691,928

(22) Filed: Oct. 23, 2003

(65) Prior Publication Data
US 2004/0138179 A1 Jul. 15, 2004

Related U.S. Application Data

(60) Provisional application No. 60/421,190, filed on Oct. 24, 2002.

(51) Int. Cl.
*A61K 31/415* (2006.01)
*A61K 31/58* (2006.01)
*A61K 31/56* (2006.01)
*A61K 9/06* (2006.01)
*A61K 9/08* (2006.01)
*A61K 9/12* (2006.01)
*A61K 9/14* (2006.01)

(52) U.S. Cl. ........ 514/396; 514/171; 514/174; 514/179; 514/182; 514/772; 424/489; 424/70.1

(58) Field of Classification Search .................. 424/514; 536/16.8; 514/396, 171
See application file for complete search history.

(56) References Cited

U.S. PATENT DOCUMENTS

| | | | |
|---|---|---|---|
| 4,895,727 A | 1/1990 | Allen | |
| 4,912,124 A | 3/1990 | Das et al. | |
| 5,002,938 A | 3/1991 | Wang et al. | |
| 5,021,458 A | 6/1991 | Maeda et al. | |
| 5,110,809 A * | 5/1992 | Wang et al. | 514/171 |
| 5,174,475 A | 12/1992 | Day et al. | |
| 5,219,877 A * | 6/1993 | Shah et al. | 514/394 |
| 5,310,545 A | 5/1994 | Eisen | |
| 5,407,663 A | 4/1995 | Eisen | |
| 5,686,089 A * | 11/1997 | Mitra et al. | 424/405 |
| 5,977,176 A * | 11/1999 | Wise et al. | 514/568 |
| 5,998,395 A * | 12/1999 | Kligman | 514/171 |
| 6,075,056 A * | 6/2000 | Quigley et al. | 514/649 |
| 6,080,744 A | 6/2000 | Ayon-Covarrubias | |
| 6,238,683 B1 * | 5/2001 | Burnett et al. | 424/405 |
| 6,395,721 B1 * | 5/2002 | Robinson et al. | 514/177 |
| 6,444,647 B1 * | 9/2002 | Robinson et al. | 514/17 |
| 2002/0165170 A1 * | 11/2002 | Wilson et al. | 514/42 |
| 2003/0232086 A1 * | 12/2003 | McCadden | 424/486 |

FOREIGN PATENT DOCUMENTS

| | | |
|---|---|---|
| EP | 1 159 956 | 12/2001 |
| WO | WO 92/18133 | 10/1992 |

OTHER PUBLICATIONS

Adams, et al., "Perianal ulcerations from topical steroid use," *Cutis* 69(1): 67-88 (2002).

Barsky, "Clinical comparison of desonide cream with fluocinonide cream in steroid-responsive dermatologic disorders," *Cutis* 18(6): 826-30 (1976).

Fleming, et al., "An inflammatory eruption associated with recombinant human IL-6," *Brit. J. Dermatol.* 130(4): 534-40 (1994).

Greenberg, et al., "Clotrimazole/betamethasone diproprionate: a review of costs and complications in the treatment of common cutaneous fungal infections," *Pediatr. Dermatol.* 19(1): 78-81 (2002).

Jorizzo, et al, "Multicenter trial for long-term safety and efficacy comparison of 0.05% desonide and 1% hydrocortisone ointments in the treatment of atopic dermatitis in pediatric patients," *J. Am. Acad. Dermatol.* 33(1): 74-7 (1995).

Lucky, et al., "Effect of desonide ointment, 0.05%, on the hypothalamic-pituitary-adrenal axis of children with atopic dermatitis," *Cutis* 59(3): 151-153 (1997).

Weinstein & Berman, "Topical treatment of common superficial tinea infections," *Am. Fam. Physician* 65(10): 2095-2102 (2002).

Fleischer et al., "Prescription of high-potency corticosteroid agents and clotrimazole-betamethasone dipropionate by pediatricians", *Clin. Ther.*, 21:1725-31 (1999).

(Continued)

*Primary Examiner* — John Pak
*Assistant Examiner* — Nathan W Schlientz
(74) *Attorney, Agent, or Firm* — Pabst Patent Group LLP

(57) ABSTRACT

A topical composition and the method using the composition, which contains an antifungal agent and a low potency anti-inflammatory steroid which is safe and effective such as desonide or its derivative. The low potency steroid agent does not cause side effects such as skin atrophy, striae and hypopigmentation. In a representative example, the low potency anti-inflammatory steroid has the following structure:

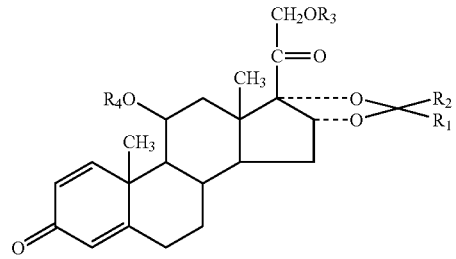

wherein $R_1$, $R_2$, $R_3$, and $R_4$ taken independently can be H, C1-C10 alkyl, C1-C10 alkenyl, C3-C10 cycloalkyl, and phenyl groups; $R_1$ and $R_2$ taken together can be C3-C10 cycloalkyl; and $R_3$, and $R_4$ taken independently can be H, C1-C10 alkyl, C1-C10 alkenyl, C3-C10 cycloalkyl, phenyl, C7-C10 phenylalkyl, carboxylate, sulfonyl, phosphoryl, and phosphonyl groups. The composition can be formulated in a dosage form such as a cream, ointment, gel, lotion, foam, powder, aerosol, spray, shampoo, or liquid solution. The composition can be used to treat a fungal disease such as tinea pedis, tinea capitis, tinea corporis, tinea versicolor, tinea cruris, and candidiasis as well as intertriginous dermatitis complicated by candidiasis.

9 Claims, No Drawings

OTHER PUBLICATIONS

Hengge, et al., *J. Am. Acad. Dermatol.* "Adverse effects of topical glucocorticosteroids", 54:1-15 (2006).

Shaffer, et al., "Use of clotrimazole/betamethasone diproprionate by family physicians", *Fam. Med.*, 32:561-5 (2000).

Smith, et al., "Nondermatologists are more likely than dermatologists to prescibe antifungal/corticosteroid products: an analysis of office visits for cutaneous fungal infections, 1990-1994", *J. Am. Acad. Dermatol.*, 39:43-47 (1998).

Stern, *J. Am. Acad. Dermatol.*, "The pattern of topical corticosteroid prescibing in the United States, 1989-1991", 35:183-6 (1996).

National Psoriasis Foundation "Potencies of topical Steroids", Jul. 1, 2004.

* cited by examiner

ANTIFUNGAL FORMULATIONS

This application claims priority to U.S. Ser. No. 60/421,190, entitled "Antifungal Formulations" filed in the U.S. Patent and Trademark Office on Oct. 24, 2002, by Jay A. Goldstein, Michael Rothman and Whe-Yong Lo.

BACKGROUND OF THE INVENTION

The present invention relates to topical formulations useful for treating fungal diseases, canidiasis, intertriginous dermatitis and their related inflammation. In particular, the present invention relates to stable topical formulations containing an antifungal agent and an anti-inflammatory steroid.

Currently, there is no topical dermatologic preparation that is appropriate for almost all of the skin conditions that are normally seen by pediatricians, internists, and dermatologists. Various formulations based on combinations of antifungals and steroids are described in U.S. Pat. Nos. 4,912,124, 5,002,938, 5,021,458, 5,110,809, 5,174,475, 5,219,877, 5,407,663, 5,310,545, 6,075,056, and 6,080,744. The disadvantage of such combinations is that it is undesirable to use fluorinated and/or potent steroids for topical treatment for extended periods of time. Steroids can penetrate the skin and cause undesirable side effects, including skin atrophy, hypopigmentation, suppression of the hypothalamic-pituitary-adrenal axis, Cushing's syndrome, and appearance of telangectasias.

Several formulations that are commercially available include Lotrisone™ cream (clotrimazole 1%/betamethasone dipropionate 0.064%), Daktacort™ cream (miconazole nitrate 2%/hydrocortisone 1%) and Canesten™ HC cream (clotrimazole 1%/hydrocortisone 1%). The steroid component, betamethasone dipropionate, Lotrisone™, is so strong that it can induce skin atrophy, striae, persistent tinea corporis and even growth retardation in children receiving Lotrisone™ treatment (see, for example, Pediatr. Dermatol. 19(1):78-81 (2002); Cutis 69(1):67-68 (2002); Am. Fam. Physician 65(10:2095-2102 (2002)). The remaining two products have only 1% hydrocortisone, which is too low in potency to have significant anti-inflammatory properties.

Therefore, there is no need for a dermatologic formulation that will cause reduced side effects but will still be potent enough for efficacy.

SUMMARY OF THE INVENTION

A topical composition has been developed which contains a low potency anti-inflammatory steroid which is safe and effective as well as an antifungal agent. The low potency steroid agent minimizes side effects such as skin atrophy, striae and hypopigmentation. In a representative example, the low potency anti-inflammatory steroid has the following structure:

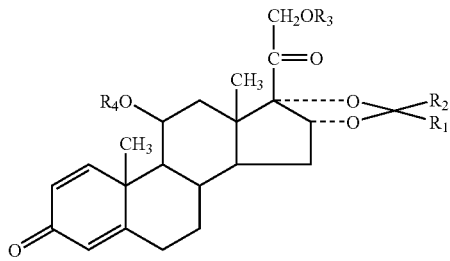

wherein $R_1$, $R_2$, $R_3$, and $R_4$ taken independently can be H, C1-C10 alkyl, C1-C10 alkenyl, C3-C10 cycloalkyl, and phenyl groups; $R_1$ and $R_2$ taken together can be C3-C10 cycloalkyl; and $R_3$, and $R_4$ taken independently can be H, C1-C10 alkyl, C1-C10 alkenyl, C3-C10 cycloalkyl, phenyl, C7-C10 phenylalkyl, carboxylate, sulfonyl, phosphoryl, and phosphonyl groups. Preferably, the $R_1$, $R_2$, $R_3$, and $R_4$ groups are independently H, $CH_3$, ethyl, propyl, phenyl, and phenylmethyl groups. More preferably, the low potency anti-inflammatory steroid is desonide and the antifungal agent is clotrimazole. Most preferably, the composition contains between 0.01 w % and 5.0 wt % desonide and between 0.1 wt % and 5.0 wt % clotrimazole.

The composition can be formulated in any dosage form suitable for topical administration. Preferably, the composition is in a form such as a cream, ointment, gel, lotion, foam, powder, aerosol, spray, shampoo, or liquid solution.

The composition has a slightly acidic pH in the range, for example, between about 3.5 to about 7.0. The composition may further include one or more solvents, emollients, humectants preservatives, emulsifiers, and/or an acid, base, or buffering agent to adjust the pH. The composition described herein may optionally contain one or more preservatives. Representative preservatives are benzyl alcohol, sodium benzoate, parabens, and any other preservative useful in drug formulation.

The compositions are useful to treat fungal diseases which are complicated by inflammation, such as tinea pedis, tinea capitis, tinea corporis, tinea versicolor, and tinea cruris. Other indications are for yeast diseases, such as candididasis and itertriginous dermatitits, in which the disease process, the presence of pathogenic yeast organisms, causes skin disease with resultant inflammation. These conditions, inflammatory tinea, tinea versicolor, and candidiasis associated with dermatitis, would respond in an accelerated fashion if both anti fungal/anti-yeast preparations were combined with an anti-inflammatory steroid. For maximum efficacy, the resultant compound is applied twice a day to the affected areas. A preferred compound would be a combination of desonide cream 0.2% and clotrimazole 1% to be applied thinly to the affected areas twice daily. Other non-halogenated or low to medium potency corticosteroids could be substituted for desonide without sacrificing efficacy. Likewise, other antifungals, such as econazole could be substituted for clotrimazole.

DETAILED DESCRIPTION OF THE INVENTION

I. Antifungal Formulation

Antifungal compositions for treating fungal infections or mycological illnesses include one or more antifungal agents as well as one or more anti-inflammatory agents. The composition also contains excipients and a pharmaceutical carrier. The useful steroid agents cause reduced side effects such as skin atrophy, perianal ulcers, striae, and skin pigmentary changes.

A. Antifungal agents

A large number of antifungal agents are known in the art. Generally, these can be generally classified into two broad categories, polyene type antifungal agents and azole type antifungal agents. Exemplary polyene type antifungal agents are, for example, Amphoterican B, Nystatin, Flucytosin, and Natamycin. Exemplary azole type antifungal agents include, for example, Ketoconazole, Econoazole, Miconazole, Itraconazole, Fluconazole, Clotrimazole, Griseofulvin, Oxiconazole, Terconazole, Tioconazole, Clotrimazole, and Silver Sulfadiazine. Other representative antifungal agents are, for example, Ciclopirox olamine, Terbinafine, and those disclosed in, for example, U.S. Pat. No. 6,075,056.

In a preferred embodiment, the antifungal agent is an azole type agent such as Clotrimazole.

B. Anti-Inflammatory Agent

In a representative embodiment, the composition includes between 0.01 wt % and 5.0 wt % non-fluorinated corticosteroid. Preferably, the non-fluorinated corticosteroid has the following structure:

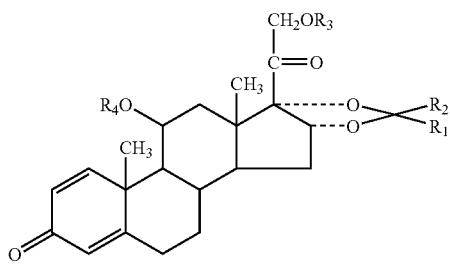

wherein $R_1$, $R_2$, $R_3$, and $R_4$ taken independently can be H, C1-C10 alkyl, C1-C10 alkenyl, C3-C10 cycloalkyl, and phenyl groups;

$R_1$ and $R_2$ taken together can be C3-C10 cycloalkyl; and $R_3$, and $R_4$ taken independently can be H, C1-C10 alkyl, C1-C10 alkenyl, C3-C10 cycloalkyl, phenyl, C7-C10 phenylalkyl, carboxylate, sulfonyl, phosphoryl, and phosphonyl groups.

Representative $R_1$, $R_2$, $R_3$, and $R_4$ groups are H, $CH_3$, ethyl, propyl, phenyl, and phenylmethyl groups.

Most preferably, the steroid is desonide. Desonide is a class 6 nonfluorinated topical corticosteroid which has been available for more than two decades. Clinical trials on desonide showed that desonide is effective and safe for treating children having dermatoses or other skin diseases (see, for example, Cutis 1997 59(3):151-153 (1997); J. Am. Acad. Dermatol. 33(1):74-7 (1995); Brit. J. Dermatol. 131(4):534-40 (1994); and Cutis 18(6):826-30 (1976)).

The composition may alternatively contain one of the following agents in a dosage that causes reduced side effects, Desoximetasone, Mometasone furoate, Triamcinolone acetonide, Triamcinolone acetate, Fluocinolone acetonide, Hydrocortisone valerate, Mometasone furoate, Clocortolone privalate, Fluticasone propionate, Hydrocortisone butyrate, Predincarbate, Aclometasone dipropionate, Desonide, Hydrocortisone probutate Hydrocortisone 1% is an OTC preparation with limited anti-inflammatory properties. It would be minimally effective, if effective at all, in treating the significant inflammation that accompanies fungal disease. Desonide is a much higher potency cortisone. It should be effective against more significant degrees of inflammation, as it is prescription only, and because it is non-fluorinated, its safety profile allows it to be used on the face, as well as in intertriginous areas, such as the axilla, the groin, and beneath the breasts, which will be typical areas of application.

C. Other Bioactive Agents

The formulation described herein optionally contains one or more other pharmaceutically active agents. Useful agents include any agents commonly used in dermatologic formulations, which may include, but are not limited to, antibacterial agents such as a tetracycline or salicyclic acid (2.0 w/w).

D. Excipients

The pharmaceutically acceptable excipients for topical administration can be a mixture of solvents, emollients, humectants, emulsifiers, and transport enhancer such as natural or synthetic polymer, and lipids.

Solvents can be, for example, alcohols, esters, propylene glycol, butylene glycol, hexylene glycol, polyethylene glycols, polypropylene glycols, polyurethane compounds, including hydroxy-terminated polyurethanes, in particular polyolprepolymer-2, polyolprepolymer-14, or polyolprepolymer-15. Emollients can be, for example, white petrolatum, mineral oil, propylene glycol dicaprylate, lower fatty acid esters and lower alkyl ethers of propylene glycol, cetyl alcohol, cetostearyl alcohol, stearyl alcohol, cetyl esters wax, spermaceti wax, white wax, isopropyl myristate, polyoxyethylene polyoxypropylene cetyl ether, polyoxypropylene methyl glucose ether, polyoxypropylene methyl glucose ether, 2-ethyl-1,3-hexanediol, propylene glycol dioctanoate, methyl gluceth-10, methyl gluceth-20, isodecyl neopentanoate, glycerin, mineral oil, etc. (preferably in an amount of up to about 40 wt %, more preferably about 5 to 30 wt %). Humectants can be, for example, glycerin and sorbitol. Emulsifiers can be, for example, glyceryl monostearate, glyceryl monoleate, polyoxyethylene cetyl ether, polyoxyethylene cetostearyl ether, polyoxyethylene stearyl ether, and polyethylene glycol stearate.

The pH is adjusted where necessary to a pH of about 3.5-7.0, using an acid e.g. hydrochloric acid phosphoric acid, or a base e.g. diethanolamine, triethanolamine, sodium hydroxide, or known buffering agents, e.g. phosphates such as monobasic sodium phosphate, and dibasic sodium phosphate, and citrates well known in the art. A preservative is generally present, for example benzyl alcohol, sodium benzoate, parabens, and the like.

Representative acids are hydrochloric acid, phosphoric acid, citric acids, and any other acids commonly used in drug formulation. Representative bases are diethanolamine, triethanolamine, sodium hydroxide, carbonate, and any other bases suitable for drug formulation.

Other excipients described in U.S. Pat. Nos. 4,912,124, 5,002,938, 5,021,458, 5,110,809, 5,174,475, 5,219,877, 5,310,545, 5,407,663, 6,075,056, and 6,080,744 are also useful for forming the composition described herein. For example, U.S. Pat. No. 4,912,124 describes a polar solvent system formed of ethanol and water.

Transport enhancers are commonly used in drug formulation to enhance the efficiency of drug delivery. For example, U.S. Pat. No. 5,219,877 discloses a vehicle system using lauryl alcohol as skin transport enhancing agent for improved antifungal activity of the drug described therein. The vehicle system of these formulations is such that both the antifungal agent and the steroid, if present, are in the solubilized state. The vehicle system consists of, in addition to lauryl alcohol, about 10 wt % to 80 wt % of a lower alkanol, such as ethanol and 0 to 40 wt % of a trihydroxy alcohol such as 1,2,6-hexanetriol. The vehicle system may be formed into a gel by using 0.1 wt % to 5 wt % of a gelling agent such as hydroxypropylcellulose or hydroxyethylcellulose).

The formulation may also contain additional materials commonly used in drug formulation, e.g., chelating agents and fragrances.

The formulations described herein can have various dosage forms. The representative dosage forms can be, for example, cream, ointment, gel, lotion, foam, powder, aerosol, spray, shampoo, or liquid solution. The formulation can be formulated into other dosages forms suitable for topical application. In one embodiment, the dosage form is one of cream, ointment, gel and lotion. In another embodiment, the dosage form is one of foam, powder, aerosol, spray, shampoo, or liquid solution. Preferably, the dosage form is cream, ointment, gel, or lotion.

Generally, the formulation will contain between 0.01 wt % and 5.0 wt % of an antifungal agent and between 0.01 wt % and 5 wt % of an anti-inflammatory steroid agent. The concentrations of the antifungal agent and the anti-inflammatory steroid can be varied according to the type of the skin conditions, the age of the patients, and the relative strength of the antifungal agents and the anti-inflammatory steroid. One of ordinary skill in the art would be able to choose an appropriate concentration for use in an appropriate age group for a particular infection.

Other additives such as fragrances and colors may also be added.

II. Method of Administration

Generally, the method using the composition described herein includes administering to a subject in need of treatment the composition in a dosage form of, form example, cream, ointment, gel, lotion, foam, powder, aerosol, spray, shampoo, or liquid solution. In one embodiment, the dosage form is one of cream, ointment, gel or lotion. In another embodiment, the dosage form is one of foam, powder, aerosol, spray, shampoo, or liquid solution.

The compositions can be used to treat any fungal disease which is complicated by inflammation. The compositions are especially useful to treat fungal diseases such as tinea pedis, tinea capitis, tinea corporis, tinea versicolor, tinea cruris, candidiasis and intertriginous dermatitis complicated by candidiasis.

We claim:

1. A topical antifungal composition comprising:
   a) a therapeutically effective amount of clotrimazole for treating a fungal disease or a pharmaceutically acceptable salt thereof; and
   b) a therapeutically effective amount of a low to low-medium potency formulation of desonide causing minimal skin atrophy, striae and hypopigmentation, in a concentration between 0.01 wt % and 5.0 wt %, and having a higher potency than 1 wt % hydrocortisone, and
   c) a carrier suitable for administration of clotrimazole and desonide to the skin, wherein the composition does not cause the desonide to penetrate the skin and cause undesirable local side effects.

2. The composition of claim 1 containing 0.1 wt % to 5 wt % clotrimazole.

3. The composition of claim 1, wherein the composition is formulated as a cream, ointment, gel, lotion, foam, powder, aerosol, spray, shampoo, or liquid solution.

4. The composition of claim 3 having a pH of about 3.5 to about 7.0 further comprising: at least one solvent, at least one emollient, at least one humectant, at least one preservative, and at least one emulsifier; and optionally including an acid, base, or buffering agent to adjust the pH.

5. The composition of claim 4, wherein the solvent is selected from the group consisting of propylene glycol, butylene glycol, hexylene glycol, polyethylene glycols, polypropylene glycols, and polyurethane compounds; the emollient is selected from the group consisting of white petrolatum, mineral oil, propylene glycol dicaprylate, lower fatty acid esters and lower alkyl ethers of propylene glycol, cetyl alcohol, cetostearyl alcohol, stearyl alcohol, stearic acid, cetyl esters wax, spermaceti wax, and white wax; the humectant is selected from the group consisting of glycerin and sorbitol; and the emulsifier is selected from the group consisting of glyceryl monostearate, glyceryl monoleate, stearic acid, polyoxyethylene cetyl ether, polyoxyethylene cetostearyl ether, polyoxyethylene stearyl ether, and polyethylene glycol stearate; wherein the optional acid is selected from the group consisting of hydrochloric acid and phosphoric acid, the optional base is chosen from diethanolamine, triethanolamine, and sodium hydroxide, the optional buffering agent is chosen from monobasic sodium phosphate and dibasic sodium phosphate, and the preservative is chosen from benzyl alcohol, sodium benzoate and parabens.

6. The composition of claim 1 wherein clotrimazole is in an amount effective to treat fungal disease selected from the group consisting of tinea pedis, tinea capitis, tinea corporis, tinea versicolor, scalp disorders, tinea cruris, and candidiasis.

7. A method of treating a fungal disease comprising administering to a subject in need of treatment the composition of any of claim 1, 2, or 3-6 with a thin application of the composition two times per day to the affected areas.

8. The method of claim 7 wherein the subject is a child of under 10 years old.

9. The method of claim 7 wherein the fungal disease is selected from the group consisting of tinea pedis, tinea capitis, tinea corporis, tinea versicolor, scalp disorders, tinea cruris, and candidiasis.

* * * * *